United States Patent
Ackley, Jr.

(10) Patent No.: US 8,037,992 B2
(45) Date of Patent: Oct. 18, 2011

(54) METHOD AND APPARATUS FOR TRANSPORTING AND PROCESSING ON-EDGE TABLETS

(75) Inventor: E. Michael Ackley, Jr., Mannington, NJ (US)

(73) Assignee: Ackley Machine Corp., Moorestown, NJ (US)

( * ) Notice: Subject to any disclaimer, the term of this patent is extended or adjusted under 35 U.S.C. 154(b) by 656 days.

(21) Appl. No.: 11/889,843

(22) Filed: Aug. 16, 2007

(65) Prior Publication Data

US 2008/0047803 A1 Feb. 28, 2008

Related U.S. Application Data

(60) Provisional application No. 60/839,136, filed on Aug. 22, 2006.

(51) Int. Cl.
*B65G 17/32* (2006.01)

(52) U.S. Cl. .......... 198/384; 198/383; 198/389

(58) Field of Classification Search .......... 198/382, 198/383, 384, 389, 392; 101/36, 37, 38.1, 101/39, 40, 40.1, 475, 485
See application file for complete search history.

(56) References Cited

U.S. PATENT DOCUMENTS

| | | | | |
|---|---|---|---|---|
| 3,884,143 A * | 5/1975 | Ackley | .......... | 101/37 |
| 4,308,942 A * | 1/1982 | Ackley | .......... | 198/380 |
| 4,335,810 A * | 6/1982 | Ackley et al. | .......... | 198/380 |
| 4,377,971 A * | 3/1983 | Ackley | .......... | 101/40 |
| 4,479,573 A * | 10/1984 | Ackley et al. | .......... | 198/399 |
| 4,632,028 A * | 12/1986 | Ackley | .......... | 101/40 |
| 4,657,130 A * | 4/1987 | Ackley et al. | .......... | 198/397.04 |
| 4,708,233 A * | 11/1987 | Nomura | .......... | 198/397.04 |
| 5,085,510 A | 2/1992 | Mitchell | | |
| 5,234,099 A * | 8/1993 | Berta | .......... | 198/867.15 |
| 5,353,456 A * | 10/1994 | Evans | .......... | 5/493 |
| 5,655,453 A * | 8/1997 | Ackley | .......... | 101/483 |
| 5,836,243 A * | 11/1998 | Ackley | .......... | 101/44 |
| 6,481,347 B2 * | 11/2002 | Ackley | .......... | 101/38.1 |
| 6,527,101 B1 * | 3/2003 | Miyamoto | .......... | 198/397.04 |
| 7,102,741 B2 * | 9/2006 | Ackley et al. | .......... | 356/237.1 |
| 7,311,045 B2 * | 12/2007 | Ackley et al. | .......... | 101/485 |

\* cited by examiner

*Primary Examiner* — Douglas Hess

(74) *Attorney, Agent, or Firm* — Nixon & Vanderhye P.C.

(57) ABSTRACT

A tablet conveying apparatus for transporting tablets includes a conveyer. Each of the tablets includes a first side, a second side opposite the first side, and a generally flat, circumferential belly band that interconnects the first and second sides. The conveyer includes a plurality of carrier bars to convey a plurality of tablets along a predetermined conveyer path. Each carrier bar has at least one pocket to receive and transport a tablet in a vertical orientation along the predetermined conveyer path. The pocket may be configured to allow rotation of the tablet about its central axis that extends transverse to the first and second sides. The pocket may be configured to establish line contact between two flat portions of the pocket and two corresponding circumferential portions along the belly band.

31 Claims, 4 Drawing Sheets

METHOD AND APPARATUS FOR TRANSPORTING AND PROCESSING ON-EDGE TABLETS

CROSS REFERENCE TO RELATED APPLICATION

This application claims the benefit of U.S. Provisional Application No. 60/839,136, filed Aug. 22, 2006, incorporated herein by reference in its entirety.

FIELD OF THE INVENTION

The present invention relates to methods and apparatuses for transporting and processing tablets, e.g., pharmaceutical tablets.

BACKGROUND OF THE INVENTION

Processing of tablets, such as inspecting, marking, and/or laser drilling of tablets, is known in the art. Inspection units are typically configured to inspect and remove tablets from a conveyer mechanism that have been improperly processed in a previous processing operation. Previous processing operations may include marking the tablets with indicia, coloring the tablets, laser drilling holes in the tablets, and/or coating the tablets. These processing operations are typically completed upstream from the inspection unit such that the inspection unit may inspect if these processes have been properly completed.

For example, a variety of known devices have been developed for applying a gel coating to pellet-shaped articles. Typically, the pellet-shaped articles, e.g., tablets, are coated by having one side of the pellet-shaped article coated at a time. Often, due to a processing error, one or both sides of the pellet-shaped article are not coated at all or one side of the pellet-shaped article is coated twice. As a result, the pellet-shaped article has at least one side that is not properly coated with gel. It is important for the manufacturer to carefully inspect the pellet-shaped articles for defects, such as an improperly coated side of the article, before the pellet-shaped article is distributed to the consumer so as to ensure the quality of the product and hence protect the safety of the consumer.

An example of an inspection unit is shown in U.S. Pat. No. 5,085,510 (the '510 patent). The '510 patent discloses an inspection unit for detecting laser drilled holes in tablets. As shown in FIG. 1, individual tablet carriers 6 are provided that transport individual tablets 2 in a vertical position past two sets of cameras 12. The cameras 12 are oriented horizontally and analyze opposing sides of the tablets 2 based on predetermined selection criteria. The cameras 12 signal a separation means 24 to divert preselected tablets 2. One significant limitation of the above unit is that only one tablet can be analyzed by a set of cameras at a time. As a result, more than one set of cameras must be utilized to maximize the inspection rate. Moreover, each tablet carrier 6 is only capable of transporting one tablet, which is inspected on both sides thereof. Thus, the '510 patent suffers in that the feed rate is severely limited because only one row of tablets is fed through the inspection unit.

Moreover, each tablet carrier 6 is configured to hold a tablet around the rim in a vertical position. This arrangement does not enable the entire exterior surface of the tablet to be inspected because at least a portion of the tablet rim and at least a portion of the tablet belly band is covered by the tablet carrier 6.

Another example of an inspection unit is disclosed in U.S. Patent Application Publication No. 2004/0094050 (the '050 publication), incorporated herein by reference in its entirety. The '050 publication discloses carrier bars provided with one or more article receiving pockets that hold the article in a horizontal position. A throughhole extends through each pocket so that the article within each pockets is visible from an upper side of the carrier bar and an inner side of the carrier bar through the throughhole. This arrangement allows cameras of the inspection unit to view both sides of the article.

Each carrier bar is configured to hold an article around the rim in a horizontal position, which does not enable the entire exterior surface of the tablet to be inspected because at least a portion of the tablet rim and at least a portion of the tablet belly band is covered by the carrier bar.

Thus, there is a need in the art for an improved method and apparatus for transporting and processing tablets that does not suffer from the above-mentioned drawbacks.

SUMMARY OF THE INVENTION

One aspect of the invention relates to a method and apparatus for transporting a plurality of tablets to facilitate processing operations.

Another aspect of the invention relates to a method and apparatus for roll-processing on-edge tablets.

Another aspect of the invention relates to a tablet conveying apparatus for transporting tablets. Each of the tablets includes a first side, a second side opposite the first side, and a belly band that interconnects the first and second sides. The tablet conveying apparatus includes a conveyer including a plurality of carrier bars to convey a plurality of tablets along a predetermined conveyer path. Each carrier bar has at least one pocket to receive and transport a tablet in a vertical orientation along the predetermined conveyer path. The pocket is configured to allow rotation of the tablet about its central axis that extends transverse to the first and second sides.

Another aspect of the invention relates to a method for processing a tablet. The method includes conveying the tablet within a carrier bar along a predetermined path, rotating the tablet with respect to the carrier bar, and performing a processing operation on the tablet while the tablet is rotating.

Another aspect of the invention relates to a carrier bar for a tablet conveying apparatus that conveys a plurality of tablets along a predetermined conveyer path. Each of the tablets includes a first side, a second side opposite the first side, and a belly band that interconnects the first and second sides. The carrier bar includes at least one pocket to receive a tablet in a vertical orientation. Each pocket is linked with a slot configured to allow a cam to engage the tablet.

Yet another aspect of the invention relates to a carrier bar for a tablet conveying apparatus to convey a plurality of tablets along a predetermined conveyer path, each of the tablets including a first side, a second side opposite the first side, and a generally flat, circumferential belly band that interconnects the first and second sides, the carrier bar comprising at least one pocket to receive one of said tablets in a vertical orientation, each said pocket including a first portion defining a ramped section having a first generally flat surface to engage a first circumferential portion of the flat belly band, and a second portion, opposite the first portion, having a second generally flat surface to engage a second circumferential portion of the flat belly band.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

The following detailed description is described in relation to several embodiments or samples of the present invention. It should be noted that one or more components/features of one embodiment can be combined with one or more components/features of another embodiment to thereby result in even further embodiments. Moreover, each single component or feature of any given embodiment alone may constitute even further embodiments.

Figure 1:
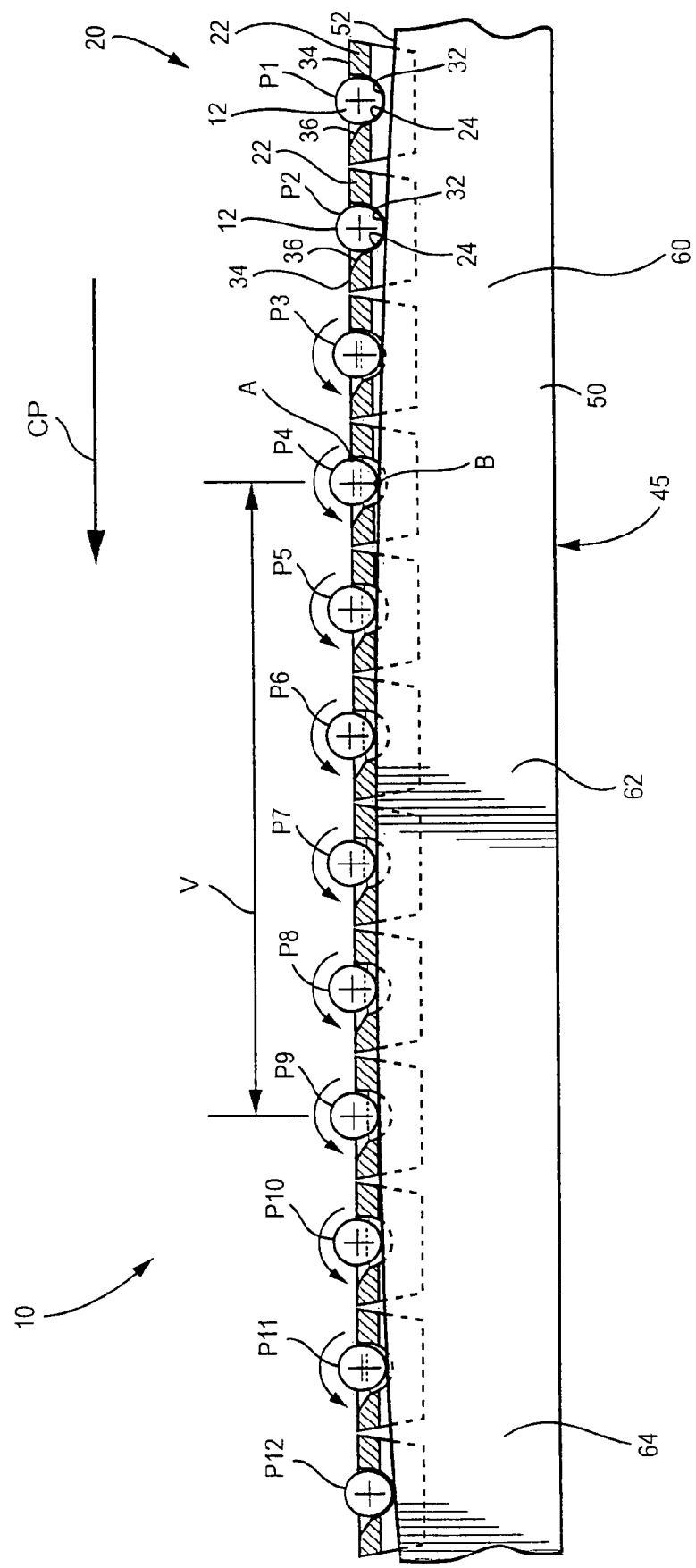
FIG. 1 is a partial cross-sectional view of an apparatus for transporting a plurality of tablets according to an embodiment of the present invention.
Figure 2:
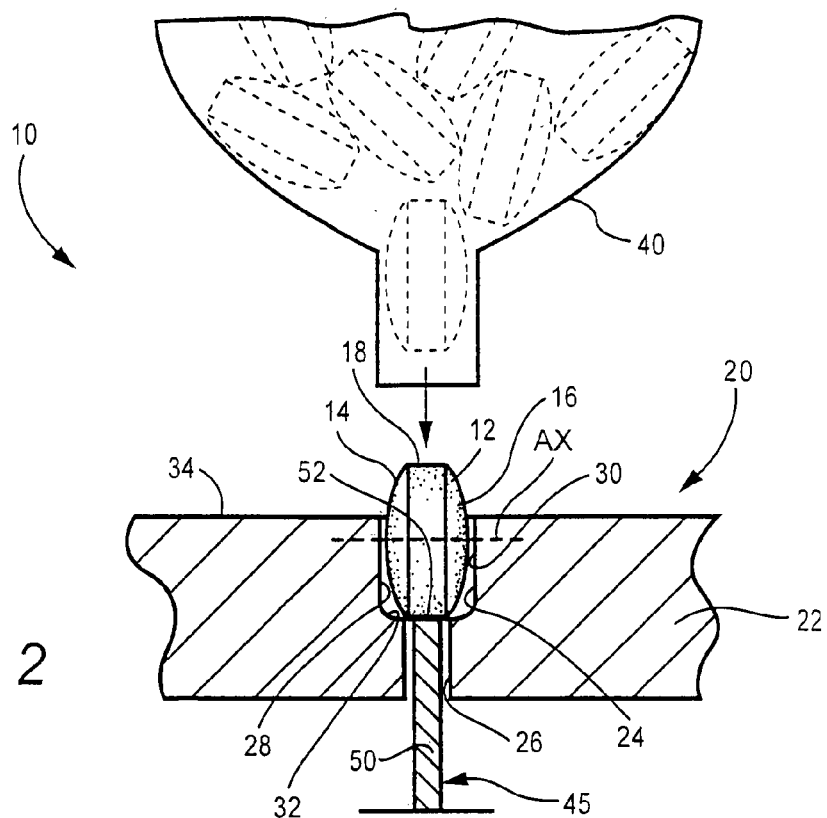
FIG. 2 is a partial cross-sectional view of the apparatus shown in FIG. 1 illustrating a tablet seated within the pocket of a carrier bar.
Figure 3:
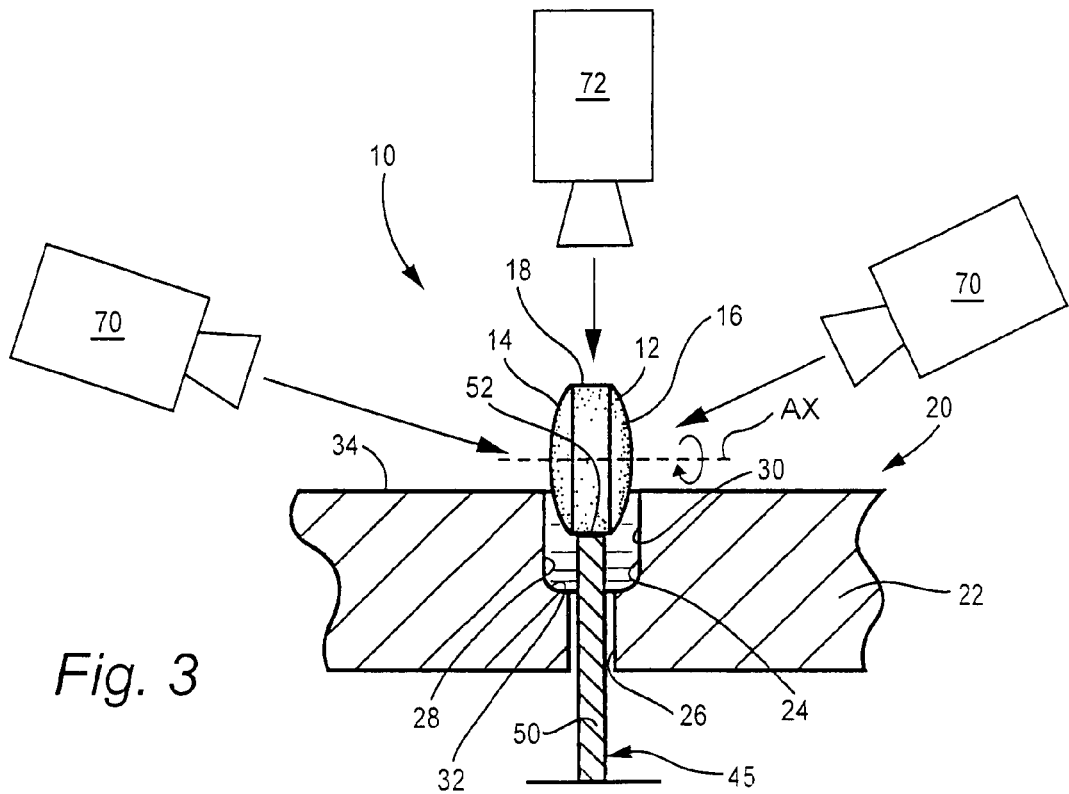
FIG. 3 is a partial cross-sectional view of the apparatus shown in FIG. 1 illustrating a tablet lifted from the pocket of a carrier bar.

FIGS. 1-3 illustrate an apparatus 10 for transporting and processing a plurality of tablets 12 according to an embodiment of the present invention. The apparatus 10 is configured to transport the plurality of tablets 12 in a manner that enables the entire exterior surface of each tablet 12 to be processed. Specifically, the apparatus 10 is configured to lift and rotate each tablet 12 with respect to its carrier bar pocket so that the entire exterior surface of each tablet 12 will be viewable or exposed for processing operations such as inspecting, marking, and/or laser drilling.

In the illustrated embodiment, the apparatus 10 is configured to transport tablets 12, e.g., pharmaceutical tablets. As best shown in FIGS. 2 and 3, each tablet 12 includes a first side 14, a second side 16 opposite the first side 14, and a belly band 18 that interconnects the first and second sides 14, 16. Each tablet 12 preferably does not have any sharp edges. The first and second sides 14, 16 may have a convex configuration, and the width of the belly band 18 may vary.

As best shown in FIGS. 1 and 2, the apparatus 10 includes a conveyer 20 including a plurality of carrier bars 22 structured to transport or convey a plurality of tablets 12 along a predetermined conveyer path CP. The conveyer 20 may be ramp-type conveyer including incline, horizontal, and decline portions as disclosed in U.S. Pat. No. 5,655,453, which is incorporated by reference in its entirety. The conveyer path CP represents the direction of travel of the carrier bars 22. Each of the carrier bars 22 is provided with one or more tablet receiving pockets 24. Each pocket 24 is linked with a respective slot 26 that extends through the carrier bar 22.

Specifically, each pocket 24 includes opposing side walls 28, 30 and a contoured bottom wall 32 that define a space in which an individual tablet 12 is to be received, e.g., crescent-shaped. The slot 26 extends transversely through the bottom wall 32 into the pocket 24. The bottom wall 32 is suitably contoured so as to conform to the circular profile of the tablet 12. Thus, the bottom wall 32 holds the tablet 12 on-edge or around a portion of the belly band 18 in a vertical position, as shown in FIGS. 1-3. The side walls 28, 30 help to maintain the tablet 12 in the vertical position.

As shown in FIG. 2, the pockets 24 of the carrier bars 22 operate to receive and entrain tablets 12 from a tablet dispenser 40, e.g., feed hopper, and move the tablets 12 along the conveyer path. The tablet dispenser 40 may be provided along an incline portion of the conveyer 20 as disclosed in U.S. Pat. No. 5,655,453. In the illustrated embodiment, the dispenser 40 may be configured to receive a supply of tablets 12 and deliver individual tablets 12 into respective pockets 24 of carrier bars 22. That is, the dispenser 40 may be structured to feed individual tablets 12 on-edge into a respective pocket 24 of a carrier bar 22. However, other feeding arrangements are possible.

As best shown in FIG. 2, when a tablet 12 is seated within its respective pocket 24, the central axis AX of the tablet 12 is positioned below the upper exterior surface 34 of the carrier bar 22. This arrangement securely maintains each tablet 12 within its respective pocket 24 as it is transported along the predetermined conveyer path CP. However, this arrangement also prevents at least a portion of the tablet 12 (e.g., the center of the tablet 12) from being viewable or exposed for processing operations. In order to view or expose the entire exterior surface of each tablet 12, i.e., including the entirety of the first and second sides 14, 16 and the belly band 18, the carrier bars 22 are conveyed past a tablet presenting assembly 45 that is configured to lift and rotate each tablet 12 with respect to its carrier bar pocket 24.

In the illustrated embodiment, the tablet presenting assembly 45 includes a stationary cam track 50. The cam track 50 is provided along the conveyer path adjacent a processing station. The cam track 50 has a predetermined length and a contoured exterior surface 52 that is adapted to engage a tablet 12. This arrangement of the exterior surface 52 varies the height of the cam track 50 along its length, which varies the presented height of the tablet 12 in use. In addition, as shown in FIGS. 2 and 3, the cam track 50 has a thickness that is sufficiently less than the width of the carrier bar slot 26 so that the cam track 50 can extend through the slot 26 and into the carrier bar pocket 24 in use.

The cam track 50 is fixedly mounted to the apparatus 10 and aligned with a respective slot 26 in the carrier bar 22. When a carrier bar 22 with multiple pockets 24 is provided, multiple cam tracks 50 will be fixedly mounted to the apparatus 10 and aligned with respective slots 26 associated with the multiple pockets 24. As the carrier bar 22 passes by the one or more cam tracks 50, the one or more cam tracks 50 will extend through respective slots 26 of the carrier bar 22, into respective pockets 24, and into engagement with the tablet 12 seated within the respective pocket 24.

The contour of the cam track 50 determines the depth at which the cam track 50 extends into the carrier bar pocket 24, and hence the height at which the tablet 12 is lifted from its carrier bar pocket 24. As illustrated, the front portion of the cam track 50 gradually slopes upwardly to provide a raise or lift section 60 that is adapted to lift the tablet 12 from the pocket 24 into an elevated position with respect to the carrier bar 24. The intermediate portion of the cam track 50 is generally flat to provide a dwell section 62 that is adapted to maintain the elevated position of the tablet 12 with respect to the carrier bar 24. The rear portion of the cam track 50 gradually slopes downwardly to provide a fall or drop section 64 that is adapted to return the tablet 12 to its seated position within the carrier bar 24. However, other cam track arrangements are possible to vary the presented height of the tablet 12.

FIG. 1 illustrates the successive movement of a tablet 12 as a carrier bar 22 passes over a cam track 50. Specifically, FIG. 1 illustrates twelve positions (represented as P1 through P12) that the tablet 12 will assume as a carrier bar 22 passes over the cam track 50.

As the carrier bar 12 reaches the raise section 60 of the cam track 50, the cam track 50 will extend through the slot 26 but will not extend into the pocket 24 and engage the tablet 12. Thus, the tablet 12 maintains its seated position within the pocket 24 at P1.

Continued movement of the carrier bar 12 along the conveyer path allows the cam track 50 to extend further through the slot 26. P2 shows the position of the tablet 12 as the cam track 50 initially engages the tablet 12.

At P3, the cam track 50 extends into the pocket 24 to lift the tablet 12 from the pocket 24 into an elevated position. The height at which the tablet 12 is lifted at P3 can be determined by the difference between the solid axis (which represents the axis of the tablet 12 in its elevated position) and the dashed axis (which represents the axis of the tablet 12 when seated within the pocket 24). As illustrated, P3 is the initial elevated position of the tablet 12 and the axis of the tablet 12 remains below the upper exterior surface 34 of the carrier bar 22.

The engagement between the cam track 50 and tablet 12 also causes rotation of the tablet 12 about its axis with respect to the carrier bar 22. Specifically, friction between the exterior surface 52 of the stationary cam track 50 and the belly band 18 of the moving tablet 12 causes rotational movement of the tablet about its axis as illustrated in FIGS. 1 and 3. To this end, the end surface of the cam track can be coated or otherwise provided with an enhanced frictional layer, e.g., rubber. The rotational movement of the tablet 12, in conjunction with its elevating position, will allow exposure of the entire tablet 12 including all of the first and second sides 14, 16 and the belly band 18.

From P4 to P5, the raise section 60 of the cam track 50 continues to lift the tablet 12 from the pocket 24 until the axis of the tablet 12 is above the upper exterior surface 34 of the carrier bar 22. Thus, by P5, at least 50% of the tablet 12 is lifted above the exterior surface 34.

The dwell section 62 of the cam track 50 maintains the elevated position of the tablet 12 with respect to the carrier bar 22. This allows the axis of the tablet 12 to be maintained above the upper exterior surface 34 of the carrier bar 22 from P6 to P9 (e.g., see FIG. 3). Moreover, the tablet 12 continues to rotate relative to the carrier bar 22.

Because of its elevated position with respect to the carrier bar 22 from about P4 to P9, at least half of the tablet 12 is visible on both sides. As the tablet 12 is rotated, the remaining half of the tablet 12 will become visible so that the entire exterior surface of the tablet 12 will be visible as the tablet 12 is moved past the cam track 50.

At P10, the carrier bar 12 reaches the drop section 64 of the cam track 50, which initiates the return of the tablet 12 to its seated position within the carrier bar 24. From P10 to P11, the downward slope of the cam track 50 lowers the tablet 12 towards its seated position within the pocket 24. At P112, the tablet 12 reaches its seated position within the pocket 24 and the cam track 50 begins to disengage from the tablet 12 as the tablet 12 continues to travel along the conveyer path CP.

The elevated position and rotating movement of the tablet 12 as it passes by the cam track 50 allows the entire exterior surface of the tablet 12 to be viewable or exposed for processing operations.

In an alternative, the tablet presenting assembly 45 may take the form of a rotating belt, drum or plurality of rollers having an outer surface that frictionally contacts and positively rotates one or preferably a plurality of tablets. The belt or drum (or rollers) can be positioned either above and/or below the carrier bars 22. Each drum or belt can contact and spin a plurality of tablets (in different rows), or there can be one-to-one correspondence between each roller/drum and each row of tablets. The belt or drum (or rollers) can be rotated together with the carrier bars (in either the same or opposite directions, depending on the desired spin direction), or the carrier bars can be held stationary during a dwell time (e.g., a second or fraction thereof) while the belt or drum spins the tablets.

As shown in FIG. 3, the processing station may include one or more cameras provided along a viewing section V adjacent the cam track 50 so that one or more surfaces of the tablet 12 may be inspected by the cameras. In the illustrated embodiment, the viewing section V extends from about P4 to P9 wherein the axis of the tablet 12 is lifted above the upper exterior surface 34 of the carrier bar 22.

For example, a side camera 70 may be positioned on one or both sides of the tablet 12 so that one or both sides 14, 16 of the tablet 12 may be inspected. Also, a top camera 72 may be provided to inspect the belly band 18 of the tablet 12. However, the side cameras 70 may be configured and arranged for viewing the belly band 18 along with the sides 14, 16 of the tablet 12.

When the tablet 12 is in its elevated position from about P4 to P9, at least 50% of the tablet 12 is above the upper exterior surface 34 of the carrier bar 22. This allows the cameras to inspect at least 50% of the exterior surface of the tablet 12, including half the first and second sides 14, 16 and half the belly band 18. However, depending on the cameras position and viewing angle, the tablet 12 may be lifted less than 50% from the carrier bar pocket 24 and still enable viewing of at least half the tablet 12. Also, the tablet 12 may be lifted less than 50% from the carrier bar pocket 24 if the center of the tablet sides 14, 16 do not need to be viewed or if the pocket size is large enough so that the cameras can view at least half of the tablet 12.

As the tablet 12 is rotated by the cam track 50, the remaining 50% of the tablet 12 will become exposed for inspection by the cameras. The cameras may be configured to inspect the tablets 12 with a line scan and/or an area scan for example. Also, the cameras may be movably mounted so that they move alongside the carrier bars 22 in the viewing section V during inspection.

The cam track 50 is preferably provided on an inclined portion of the conveyer 20. This positioning allows gravity to force the tablet 12 against the back portion of the bottom wall 32 of the carrier bar pocket 24 as the carrier bar 22 travels past the cam track 50. Specifically, the back portion of the bottom wall 32 pushes the tablet 12 and creates a two-point contact for control, i.e., point A at the back portion of the bottom wall 32 and point B at the cam track 50 as shown in FIG. 1. This arrangement maintains the tablet 12 in a pocket 24 and allows the tablet 12 to rotate. However, the cam track 50 may be provided on a horizontal portion or declining portion of the conveyer 20 for example.

As illustrated, the front portion of the bottom wall 32 includes a chamfer 36 to facilitate removal of the tablet 12 from the pocket 24 when the carrier bar 22 is rotated to dump or discharge the tablet 12 from the pocket 24, e.g., following inspection.

Figure 4:
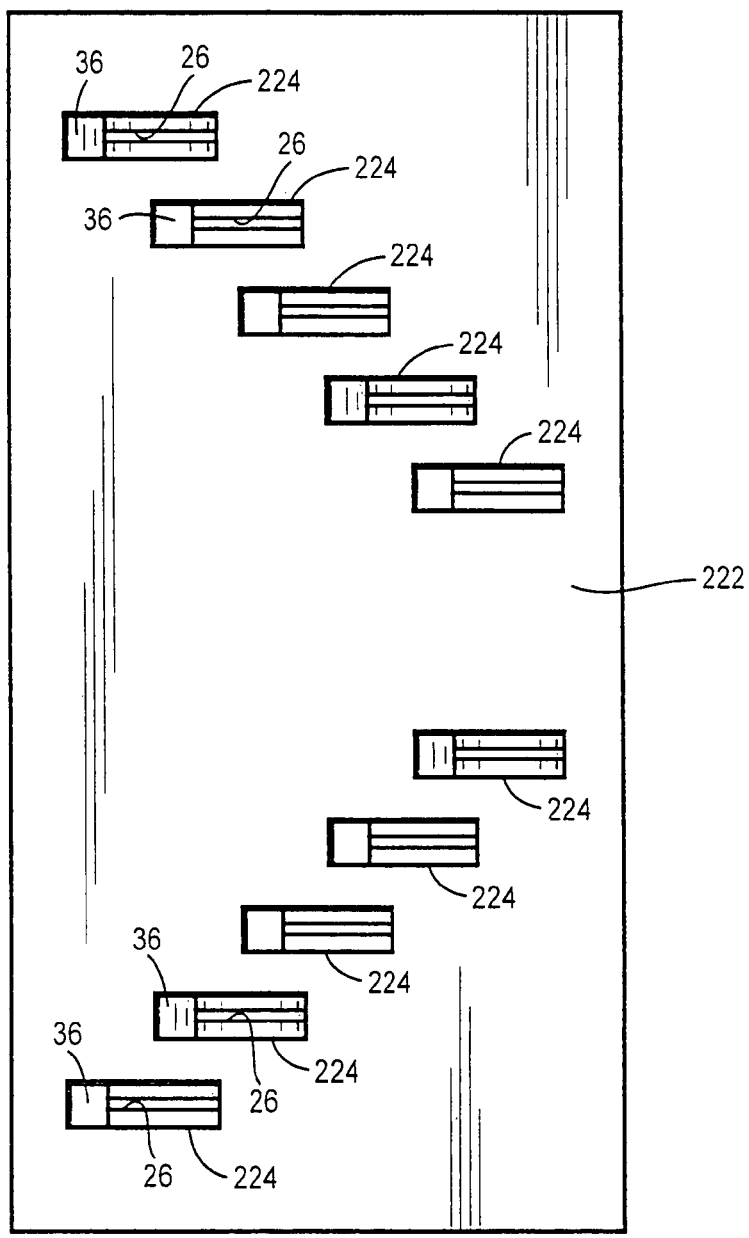
FIG. 4 is a top view of a carrier bar including staggered pockets according to an embodiment of the present invention.
Figure 5:
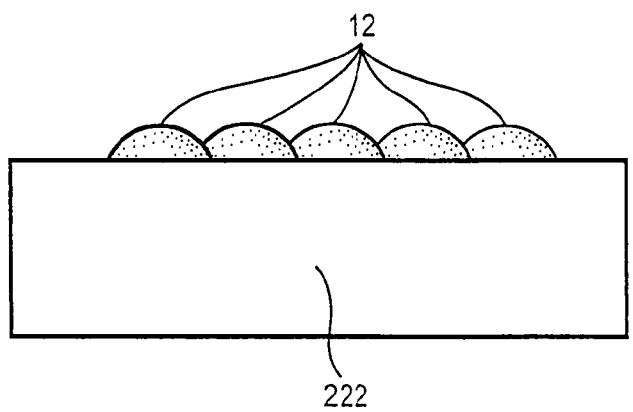
FIG. 5 is a side view of the carrier bar shown in FIG. 4 illustrating tablets seated within respective pockets of the carrier bar.

Each carrier bar 22 may have a single pocket 24 or may have a plurality of pockets 24 disposed along its length. For example, FIGS. 4 and 5 illustrate a carrier bar 222 having a number of staggered pockets 224 provided along its length. This arrangement allows multiple tablets 12 to be viewed at one time, and the hidden portion of the tablets 12 due to tablet overlap (as shown in FIG. 5) will be viewable due to the rotating movement of the tablets 12 in use.

In the embodiment described above, the processing station is in the form of an inspection unit having one or more cameras. However, it should be understood that the tablets 12 may be exposed in a manner as described above for other processing operations. For example, the tablets 12 may be exposed in a manner as described above for printing and/or laser operations. Specifically, the tablet 12 may be entirely exposed to allow performance of a printing and/or laser operation on any portion of the tablet 12.

Also, in the illustrated embodiment, the tablet presenting assembly 45 includes a stationary cam track 50 that is configured to lift and rotate each tablet 12 with respect to its carrier bar pocket 24. However, the tablet presenting assembly 45 may have other suitable arrangements to present or expose the tablet 45.

In an embodiment, the tablet presenting assembly 45 may be configured to lift and/or rotate the tablet 12. Thus, lifting and/or rotating depends on the user's desired view of the tablet. For example, the user may want to view the belly band of the tablet only. In such an arrangement, the tablet presenting assembly 45 may be a stationary cam track that engages the tablet but does not substantially lift the tablet from the pocket. This rotates the tablet to allow viewing of the entire belly band, but lifting is not provided as viewing the entire side is not needed.

In another embodiment, the tablet presenting assembly 45 may be configured to slightly lift, e.g., lift the tablet to expose less than 50% of the side of the tablet, and rotate the tablet 12. This arrangement may be used when the user needs to view only a portion of the side of the tablet, e.g., not the center of the tablet side. Thus, the degree of lift provided by the tablet presenting assembly 45 may be selected based on the user's desired view of the tablet.

In yet another embodiment, the tablet presenting assembly 45 may include an electronic solenoid to present the tablet. In another embodiment, the tablet presenting assembly 45 may include a magnetic arrangement, e.g., same or opposite poles, to present the tablet. However, other suitable arrangements are possible for presenting the tablet.

The tablet presenting assembly 45 may be incorporated into an intermittent system. For example, while the carrier bar is stopped, a tablet presenting assembly 45 in the form of a rotating roller may be moved into engagement with the tablet within the carrier bar to at least rotate the tablet with respect to the carrier bar. This arrangement allows viewing of the tablet when the carrier bar is in a stopped position.

In still another embodiment, each carrier bar may have a contoured tablet receiving pocket. The contoured pocket would provide different pocket depths for varying the presented height of the tablet. For example, the pocket may have a relatively deep region that encloses a substantial portion of the tablet, e.g., encloses more than 50%, and a relatively shallow region that exposes a substantial portion of the tablet, e.g., exposes more than 50%. The tablet may be moved by gravity between the relatively deep and shallow regions, e.g., supported within the relatively shallow region during an incline portion of the conveyer and movable to the relatively deep region during a horizontal portion of the conveyer. This pocket arrangement may be used for "lifting" the tablet, and a cam may be engaged with the tablet for rotating the tablet.

Figure 6:
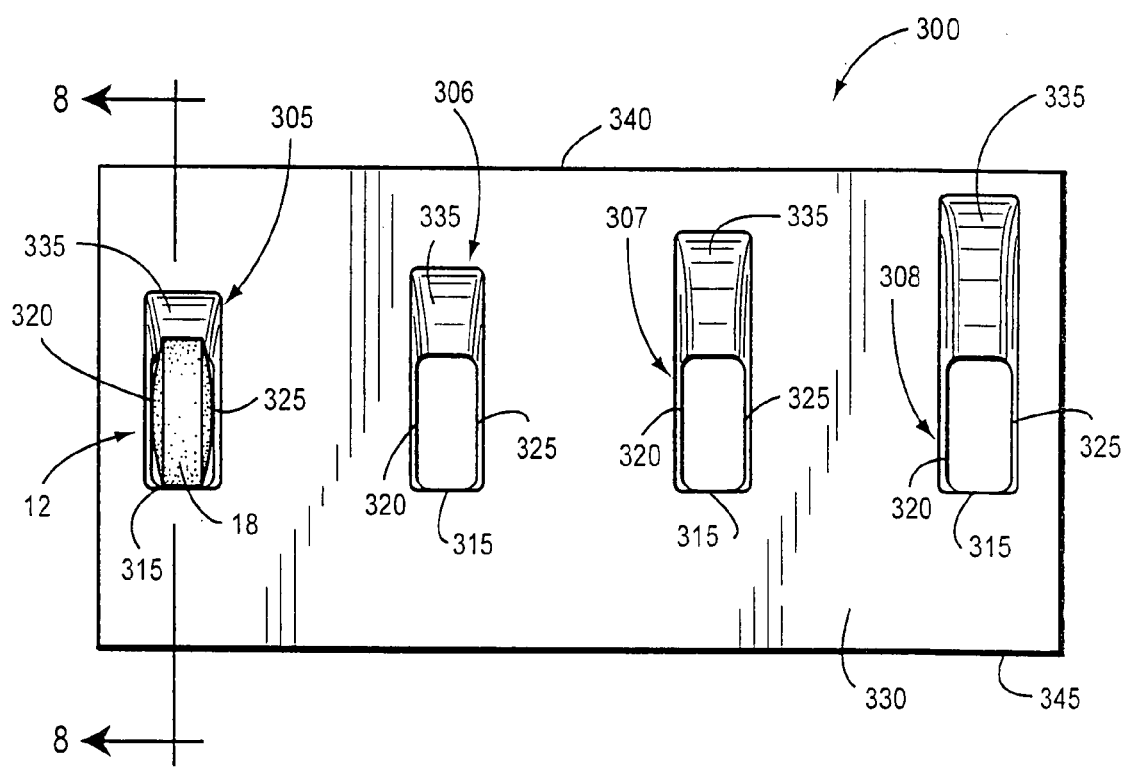
FIG. 6 is a top view of a sample carrier bar showing a plurality of pockets according to embodiments of the present invention.
Figure 7:
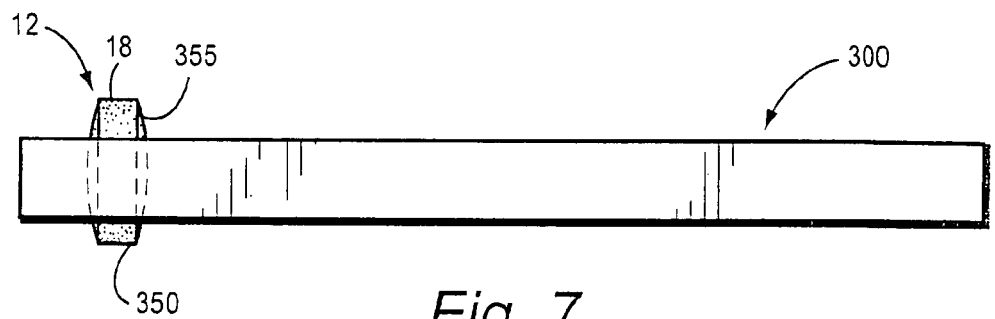
FIG. 7 is a front view of the carrier bar of FIG. 6.
Figure 8:
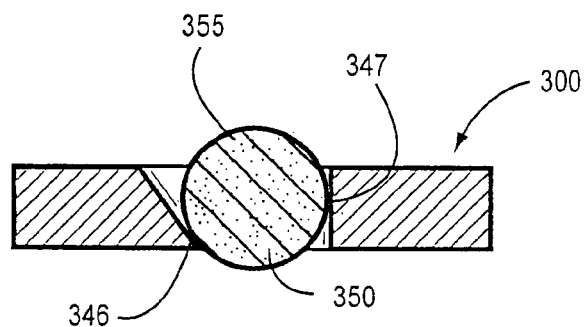
FIG. 8 is a cross sectional view along line 8-8 in FIG. 6.

FIGS. 6-8 illustrate a sample carrier bar 300 with a plurality of pockets 305, 306, 307 and 308 each adapted to receive a tablet 12 having a belly band 18. While the pockets in the carrier bar 300 would normally all have the same shape, FIG. 6 illustrates a number of potential shapes that the carrier bar 300 may have. Each pocket 305, 306, 307, 308 includes a front wall 315 and side walls 320, 325 that are generally perpendicular to an upper surface 330 of the carrier bar. The side walls 320, 325 may be chamfered or tapered adjacent the upper surface 330 to facilitate introduction of the tablets 12 into the pockets 300. In addition, each pocket 300 includes a ramped or inclined surface 325 that, together with the front wall and side walls, define an aperture, e.g., a generally rectangular aperture. Pocket 308 has the most gradual ramped surface, while pocket 305 has the steepest ramped surface. The ramp angle generally varies from about 10-80°, although the ramp angle for pocket 305 is about 50-60°. The ramp can even extend past an edge 340 of the carrier bar. The ramped surface can be made even more gradual by moving the aperture towards the opposite edge 345 of the carrier bar 300.

The belly band 18 of the tablet is generally flat. The pocket is configured so as to have two flat contact portions that support the tablet in a stable manner (e.g., using line contact). The flat surfaces (e.g., ramp surface 346 and opposite surface 347) of the pocket contact the flat surface of the belly band in two circumferential locations (e.g., about 3 o'clock and about 7-8 o'clock as shown in FIG. 8). The flat surface contact results in line contact (v. point contact) to help stabilize the tablet during processing, e.g., prevent rocking. A small clearance is provided on the sides of the tablet relative to the sides of the pocket to allow entry/exit of the tablet into the pocket.

The carrier bar, including the pockets, can be machined or made by some other process, such as stereo lithography or PolyJet, both commercially available. Each carrier bar 300 may include one or more pockets, e.g., 2-20 pockets or more, such as about 12 pockets.

The carrier bar 300 and the pocket are designed in this example so that the tablet may protrude from the bottom and top sides of the carrier bar. During processing, e.g., during printing, the printer (such as a contact printer) may impart a force against the tablet that wedges it into the pocket. To loosen the tablet after processing, a stationary member may be provided on the conveyer and arranged to contact or "tick" the bottom 350 of tablet. Other dislodging structure is also possible, such as a jet, etc. The tablet need not be rotatable in the pocket, although the bottom portion 350 can also serve to rotate against a cam surface, etc., as described above.

The carrier bar/pocket may also be arranged so that the top 355 of the tablet extends from the top of the carrier bar. This is advantageous since it presents an exposed surface that can easily be processed. In addition, the upward protrusion can be advantageous during the tablet loading step, e.g., where a hopper is located. In contrast to the hopper 40 shown in FIG. 2, the hopper can be configured to receive a number of tablets in random order, in which the hopper has a bottom opening that places a plurality of tablets in communication with the upper surfaces of a plurality of carrier bars. Once the tablet is seated within the pocket while in the hopper, the top of the tablet that is exposed can then contact the remaining non-seated tablets in the hopper. The result is that the non-seated tablets are agitated or otherwise moved, which in turn helps to seat these tablets when the next vacant carrier bar pocket proceeds through the hopper.

As shown in FIG. 7, the carrier bar has a generally rectangular configuration, where the tablet protrudes from both the top and bottom of the carrier bar. However, the carrier bar could also have a number of grooves on the bottom surface thereof, like shown in FIG. 2. The grooves can be the same width as the side walls of the pocket, to facilitate manufacturing. The grooves can extend from one edge to the opposite edge, such that the side view would have a tooth-like design on the bottom edge thereof.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. A tablet conveying apparatus for transporting tablets, each of the tablets including a first side, a second side opposite the first side, and a belly band that interconnects the first and second sides, the tablet conveying apparatus comprising:
   a conveyer including a plurality of carrier bars to convey a plurality of tablets along a predetermined conveyer path, each carrier bar having at least one pocket to receive and transport a tablet in a vertical orientation along the predetermined conveyer path,
   wherein, when the tablet is in the vertical orientation, the pocket is configured to allow rotation of the tablet about its central axis that extends transverse to the first and second sides and which axis is generally parallel to leading and trailing edges of the carrier bar, and
   wherein the tablet presenting assembly includes a cam track that varies a height at which the tablet is lifted from the pocket.

2. The tablet conveying apparatus according to claim 1, wherein each pocket is linked with a slot that extends through the carrier bar.

3. The tablet conveying apparatus according to claim 2, further comprising a tablet presenting assembly provided along the conveyer path, the tablet presenting assembly adapted to extend through the slot, into the pocket, and into engagement with the tablet as the carrier bar is transported past the tablet presenting assembly.

4. The tablet conveying apparatus according to claim 3, wherein the tablet presenting assembly includes a contoured exterior surface adapted to engage the tablet, the contoured exterior surface configured to lift and/or rotate the tablet with respect to the pocket.

5. The tablet conveying apparatus according to claim 3, wherein the tablet presenting assembly is provided along an inclined portion of the conveyer.

6. The tablet conveying apparatus according to claim 1, wherein the cam track includes a raised section to lift the tablet from the pocket into an elevated position, a dwell section to maintain the elevated position of the tablet, and a fall section to return the tablet to its seated position within the pocket.

7. The tablet conveying apparatus according to claim 1, wherein the cam track is adapted to lift the tablet such that at least 50% of the tablet is exposed from the pocket.

8. The tablet conveying apparatus according to claim 1, wherein the cam track is adapted to lift the tablet such that the central axis of the tablet is above an upper exterior surface of the carrier bar.

9. The tablet conveying apparatus according to claim 1, further comprising at least one processing operation along the conveyer, the at least one processing operation including inspecting, marking, and/or laser drilling.

10. The tablet conveying apparatus according to claim 1, wherein the at least one pocket includes a plurality of pockets staggered along a length of the carrier bar.

11. The carrier bar according to claim 1, wherein each pocket includes a crescent shape.

12. The tablet conveying apparatus according to claim 1, wherein the pocket is configured to expose the entire belly band to processing as a result of rotation of the tablet about its central axis.

13. A method for processing a tablet, comprising:
   conveying the tablet in a vertical orientation within a carrier bar along a predetermined path;
   rotating the tablet with respect to the carrier bar; and
   performing a processing operation on the tablet while the tablet is rotating.

14. The method according to claim 13, wherein performing a processing operation includes inspecting the tablet with at least one camera.

15. The method according to claim 13, further comprising:
   lifting the tablet with respect to the carrier bar; and
   performing a processing operation on the tablet while the tablet is lifted.

16. The method according to claim 15, wherein lifting the tablet includes lifting the tablet such that at least 50% of the tablet is exposed from the pocket.

17. The method according to claim 15, further comprising varying a height at which the tablet is lifted with respect to the carrier bar.

18. A carrier bar for a tablet conveying apparatus that conveys a plurality of tablets along a predetermined conveyer path, each of the tablets including a first side, a second side opposite the first side, and a belly band that interconnects the first and second sides, the carrier bar comprising:
   at least one pocket to receive a tablet in a vertical orientation, each pocket being linked with a slot extending through a bottom wall of the pocket and configured to allow a tablet presenting assembly to engage the tablet, the slot extending along a lower surface of the carrier bar and from a front edge to a rear edge of the carrier bar, substantially parallel to a direction of conveyance of the carrier bar.

19. The carrier bar according to claim 18, wherein the at least one pocket includes a plurality of pockets staggered along a length of the carrier bar.

20. The carrier bar according to claim 18, wherein each pocket includes a crescent shape.

21. The carrier bar according to claim 18, wherein the pocket is configured to allow rotation of the tablet about its central axis that extends transverse to the first and second sides.

22. A carrier bar for a tablet conveying apparatus to convey a plurality of tablets along a predetermined conveyer path, each of the tablets including a first side, a second side opposite the first side, and a generally flat, circumferential belly band that interconnects the first and second sides, the carrier bar comprising a generally rectangular main body having a generally flat upper surface and at least one pocket formed in the generally flat surface, the at least one pocket being structured to receive one of said tablets in a vertical orientation such that a longitudinal axis extending from the first side to the second side of the tablet is generally perpendicular to a conveying direction of the carrier bar, each said pocket including a first portion defining a ramped section having a first generally flat surface to establish line contact with a first circumferential portion of the flat belly band while the tablet is in the vertical orientation, and a second portion, opposite the first portion, having a second generally flat surface to establish line contact with a second circumferential portion of the flat belly band while the tablet is in the vertical orientation, wherein the pocket is configured to allow a top portion of the tablet to project above the generally flat upper surface such that the belly band and first and second sides are exposed for processing.

23. The carrier bar according to claim 22, wherein the pocket is configured to support the tablet with a portion extending above an upper surface of the carrier bar.

24. The carrier bar according to claim 22, wherein the pocket includes a pair of side walls that together with the ramped section and the first and second generally flat surfaces define an aperture extending through the carrier bar.

25. The carrier bar according to claim 24, wherein the aperture is generally rectangular.

26. The carrier bar according to claim 24, wherein the aperture is sized and dimensioned to support the tablet with a portion extending below a lower surface of the carrier bar.

27. The carrier bar according to claim 22, wherein the ramped section is angled in the range of about 10-90 degrees relative to horizontal.

28. The carrier bar according to claim 27, wherein the ramped section is angled between about 50-60 degrees.

29. A tablet conveying apparatus for transporting tablets comprising a conveyer including a carrier bar according to claim 22.

30. The carrier bar according to claim 22, wherein the tablet, while in the vertical orientation, contacts only the first and second circumferential portions of the side belly band.

31. The carrier bar according to claim 22, wherein the tablet is circular in cross section, and wherein the first circumferential portion is positioned to engage the tablet at about 3 o'clock, and the second circumferential portion is positioned to engage the tablet at about 7-8 o'clock.

* * * * *